(12) United States Patent
VanWiggeren et al.

(10) Patent No.: US 7,684,024 B2
(45) Date of Patent: Mar. 23, 2010

(54) SWEPT-ANGLE SPR MEASUREMENT SYSTEM

(75) Inventors: Gregory D. VanWiggeren, San Jose, CA (US); Douglas M. Baney, Los Altos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 290 days.

(21) Appl. No.: 11/941,769

(22) Filed: Nov. 16, 2007

(65) Prior Publication Data

US 2009/0180105 A1 Jul. 16, 2009

Related U.S. Application Data

(63) Continuation of application No. 10/977,669, filed on Oct. 29, 2004, now Pat. No. 7,317,519.

(51) Int. Cl.
*G01N 21/41* (2006.01)
*G01N 21/55* (2006.01)

(52) U.S. Cl. .................... 356/128; 356/135; 356/445

(58) Field of Classification Search ......... 356/445–448, 356/237.2
See application file for complete search history.

(56) References Cited

U.S. PATENT DOCUMENTS

| 5,012,464 | A | | 4/1991 | Vedder et al. | |
|---|---|---|---|---|---|
| 5,374,563 | A | * | 12/1994 | Maule | 436/165 |
| 5,841,570 | A | | 11/1998 | Velsko | |
| 6,417,925 | B1 | * | 7/2002 | Naya | 356/445 |
| 6,636,301 | B1 | | 10/2003 | Kvamme et al. | |
| 6,752,963 | B2 | * | 6/2004 | Dickopf et al. | 422/82.09 |
| 6,862,094 | B2 | * | 3/2005 | Johansen | 356/445 |
| 6,879,401 | B2 | * | 4/2005 | Gedig | 356/445 |
| 2001/0026943 | A1 | | 10/2001 | Dickopf et al. | |
| 2003/0011745 | A1 | | 1/2003 | Molebny et al. | |
| 2003/0063257 | A1 | | 4/2003 | Molebny | |
| 2003/0090668 | A1 | * | 5/2003 | Naya et al. | 356/445 |
| 2004/0042014 | A1 | | 3/2004 | Feldman | |
| 2004/0201849 | A1 | * | 10/2004 | Codner et al. | 356/445 |

FOREIGN PATENT DOCUMENTS

| CN | 1364233 | 11/2001 |
|---|---|---|
| EP | 0 503 236 | 9/1992 |
| GB | 2 184 321 | 6/1987 |
| WO | 92 18845 | 10/1992 |
| WO | 96 02823 | 2/1996 |
| WO | 9602823 | 2/1996 |
| WO | 00 19885 | 4/2000 |

(Continued)

OTHER PUBLICATIONS

European Search Report dated Oct. 5, 2006; pp. 1-3.

(Continued)

*Primary Examiner*—Gregory J Toatley, Jr.
*Assistant Examiner*—Jarreas C Underwood
(74) *Attorney, Agent, or Firm*—John L. Imperato

(57) ABSTRACT

A swept-angle SPR measurement system deflects an optical beam over a range of deflection angles according to a control signal and maps the deflected beam to a target within a range of incidence angles that corresponds to the range of deflection angles.

20 Claims, 4 Drawing Sheets

FOREIGN PATENT DOCUMENTS

WO        0019885        4/2000

OTHER PUBLICATIONS

S. G. Nelson, K. S. Johnston, S. S Yee—"High Sensitivity Surface Plasmon Resonance Sensor Based On Phase Detection", Elsevier Science S. A.; Sensors and Actuators B 35-36 (1996); pp. 187-191.

Charles E. H. Berger, Jan Greve—"Differential SPR Immunosensing"; Elsevier, Sensors And Actuators B 63 (2000); pp. 103-108.

Sergey I. Bozhevolnyi, Brian Vohnsen, Igor I. Smolyaninov, Anatoly V. Zayats—"Direct Observation Of Surface Polariton Localization Caused By Surface Roughness"; Elsevier, Jun. 15, 1995, Optics Communications 117 (1995); pp. 417-423.

Philippe Guedon, Thierry Livache, Francoise Martin, Frederic Lesbre, Andre Roget, Gerard Bidan and Yves Levy—"Characterization And Optimization Of A Real-Time, Parallel, Label-Free, Polypyrrole-Based DNA Sensor By Surface Plasmon Resonance Imaging"; Analytical Chemistry, vol. 72, No. 24, Dec. 15, 2000; pp. 6003-6009.

* cited by examiner

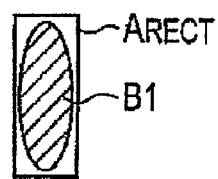
Figure 4A   Figure 4B
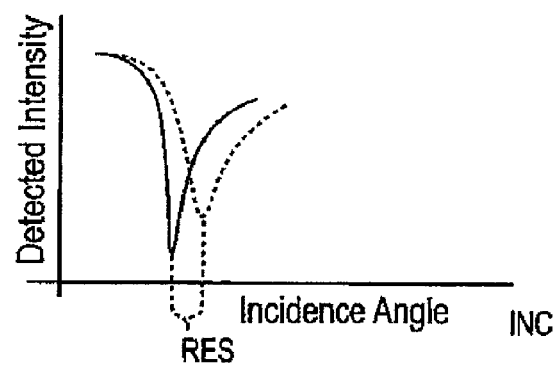
Figure 5A
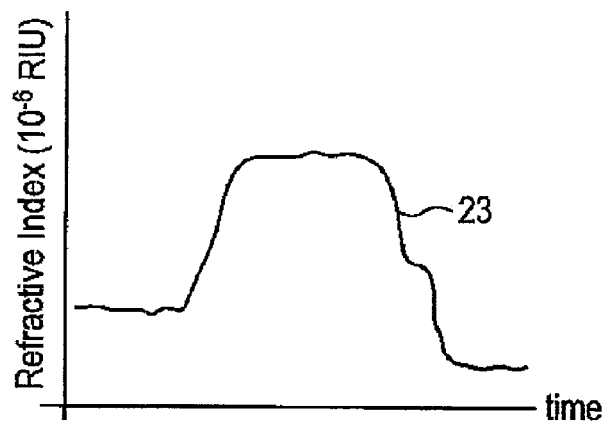
Figure 5B

SWEPT-ANGLE SPR MEASUREMENT SYSTEM

CROSS-REFERENCE TO RELATED APPLICATIONS

This application is a continuation of prior application Ser. No. 10/977,669, filed 29 Oct. 2004 now U.S. Pat. No. 7,317,519.

BACKGROUND OF THE INVENTION

Surface plasmon resonance (SPR) measurement systems rely on surface plasmon resonances to detect changes in refractive index of a target at a transducing interface. Due to the surface plasmon resonance phenomenon, optical signals that are incident on the transducing interface undergo a loss at a resonant incidence angle. Changes in the refractive index of the target cause changes in the resonant incidence angle that can be detected by measurements of the intensity of optical signals that are deflected by the target. An SPR measurement system relates detected changes in the resonant incidence angle to corresponding changes in the refractive index of the target, typically in the form of an SPR sensorgram, which is a plot of the relative refractive index of the sample versus time. SPR sensorgrams can be used to characterize biochemical processes at the transducing interface based on relationships between the biochemical processes and refractive indices of the targets at the transducing interface.

A prior art SPR measurement system (shown in FIG. 1) detects shifts in resonant incidence angle by measuring the intensity of the optical signals deflected by the target while mechanical actuators rotate the target over an angular adjustment range +/−2.5 degrees to vary the incidence angle of the target relative to an incident optical beam. Because some biochemical processes can produce shifts in resonant incidence angle of less than $10^{-4}$ degrees, it may be desirable for the SPR measurement system to have capability to measure small shifts in resonant incidence angle that are induced by changes in refractive index. In addition, it may be desirable for angular rotation of the target to occur at high repetition rates to detect biochemical processes of short duration at the transducing interface. However, the precision of the measurements of the resonant incidence angle, and the repetition rates for detecting biochemical processes at the transducing interface are limited by the mechanical actuators used in the SPR measurement system to provide the angular rotations of the target.

SUMMARY OF THE INVENTION

A swept-angle SPR measurement system according to embodiments of the present invention deflects an optical beam over a range of deflection angles according to a control signal and maps the deflected beam to a target within a range of incidence angles that corresponds to the range of deflection angles.

BRIEF DESCRIPTION OF THE DRAWINGS

FIGS. 4A-4B show optical beams incident on an optical aperture of an acousto-beam deflector.

FIG. 5A one example of a shift in resonant incidence angle detected by the swept-angle SPR measurement system according to embodiments of the present invention.

FIG. 5B shows one example of an SPR sensorgram provided by the swept-angle SPR measurement system according to embodiments of the present invention.

DETAILED DESCRIPTION OF THE EMBODIMENTS

Figure 2:
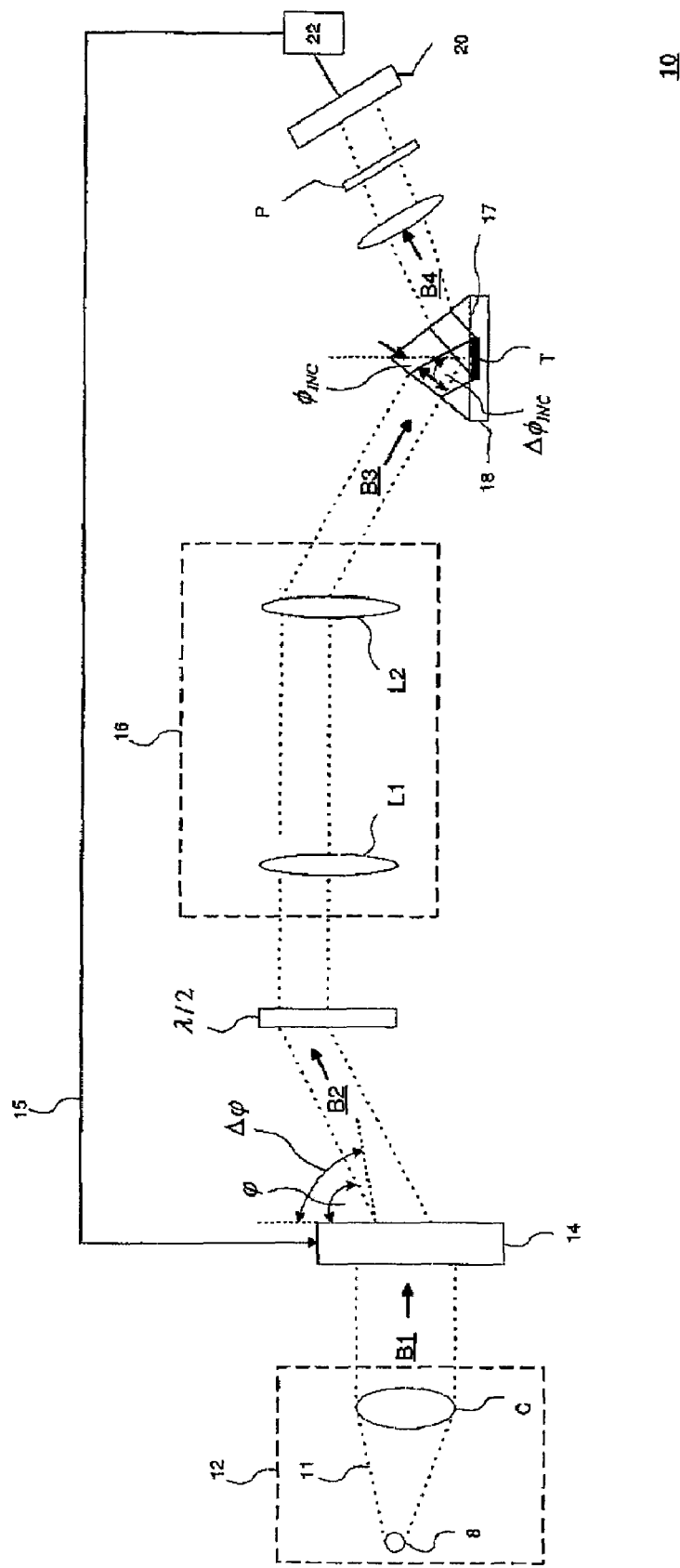
FIG. 2 shows a swept-angle SPR measurement system according to embodiments of the present invention.

FIG. 2 shows a swept-angle SPR measurement system 10 according to embodiments of the present invention. The swept-angle SPR measurement system 10, hereinafter "measurement system 10", includes an optical source 12, a beam deflector 14, and an imaging telescope 16 that directs optical beams provided by the beam deflector 14 to a target T.

Figure 1:
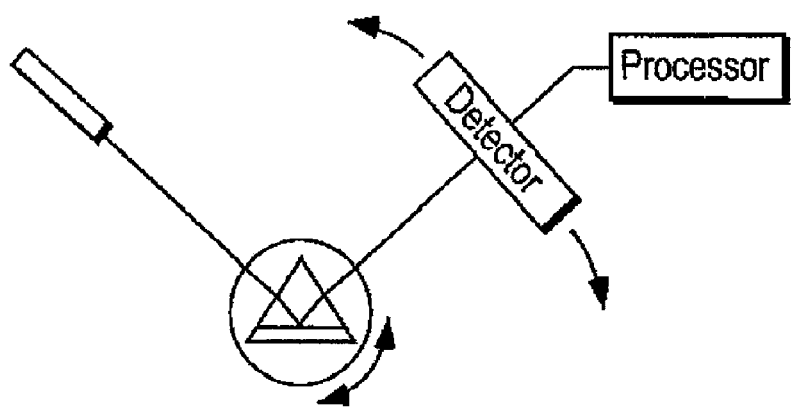
FIG. 1 shows a prior art SPR measurement system.
Figure 3:
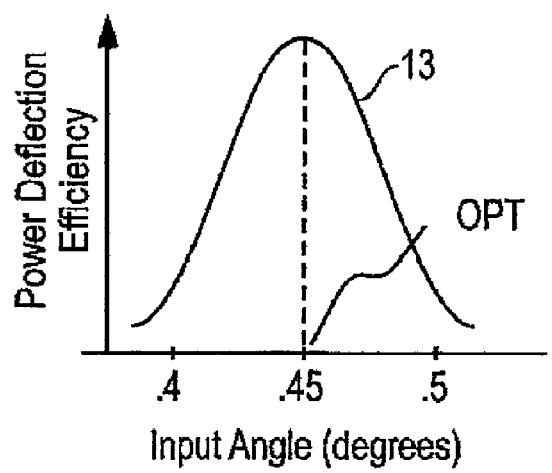
FIG. 3 shows one example of a response characteristic of an acousto-beam deflector suitable for inclusion in the swept-angle SPR measurement system of FIG. 1.

The optical source 12 provides a collimated optical signal, designated as optical beam B1. Typically, the optical source 12 includes an LED, a laser, or a superluminescent light source. The optical source 12 can provide an optical signal 11 having a single wavelength, multiple wavelengths, or wavelengths that are selectable. However, the optical source 12 can include any other type of emitter 8 suitable for providing an optical signal 11 having sufficiently stable wavelength and intensity characteristics over a measurement acquisition interval of the measurement system 10, so as not to corrupt measurements that are acquired by the measurement system 10. When the optical signal 11 provided by the emitter 8 is not collimated, the optical source 12 includes a collimator C cascaded with the emitter 8 to collimate the optical beam B1. The beam deflector 14 may have a narrow range of incident angles within which incident optical beams, such as the optical beam B1, are efficiently deflected. Collimating the optical beam B1 prevents the optical beam B1 from diverging from an optimum input angle $a_{OPT}$, improving the efficiency of the beam deflector 14 and raising the optical power of deflected beams B2 that are provided by the beam deflector 14. FIG. 3 shows one example of an efficiency contour 13 associated with the beam deflector 14, indicating that even slight deviations from the optimum input angle $a_{OPT}$ can substantially decrease relative optical power in the deflected beams B2 that are provided by the beam deflector 14 due to decreases in power deflection efficiency that accompany deviations from the optimum input angle $a_{OPT}$. For a typical beam deflector 14, collimation of the optical beam B1 in the plane that contains the deflection angle f of the deflected beam B2 is sufficient to provide efficient deflection of the optical beam B1 by the beam deflector 14. However, the collimator C typically includes elements to also collimate the optical beam B1 in a direction orthogonal to the plane that contains the deflection angle f of the deflected beam B2.

The collimator C can also transform the shape of the optical signal 11 provided by the emitter 8 so that the optical beam B1 provided by the optical source 12 accommodates the dimensional aspects of an optical aperture associated with the beam deflector 14. Typically, the collimator C shapes and sizes the optical beam B1 to be consistent with the optical aperture of the beam deflector 14. This enables efficient transfer of optical power from the optical beam B1 to the deflected beam B2. In one example the emitter 8 provides an optical signal 11 that has a circular shape, and the optical aperture of the beam deflector 14 is rectangular. In this example, the collimator C includes one or more cylindrical lenses to transform the circular shape of the optical signal 11 to an elliptical shape in the optical beam B1. The elliptical shape accommodates the rectangular optical aperture $A_{RECT}$ of the beam deflector 14 as shown in FIG. 4A. In another example, the optical aperture of the beam deflector 14 is rectangular and the emitter 8 provides an optical signal 11 that has an elliptical shape. In this example, the collimator C can include one or more spherical lenses to collimate the optical signal 11 into an optical beam B1 that accommodates the rectangular optical aperture $A_{RECT}$ of the optical detector 14 as shown in FIG. 4A. In another example, the emitter 8 provides an optical signal 11 that has a circular shape and the optical aperture of the beam deflector 14 is square. In this example, the collimator C can include one or more spherical lenses to collimate the optical signal 11 into the optical beam B1 that accommodates the square optical aperture $A_{SQ}$ of the beam deflector 14 shown in FIG. 4B. In another example, the optical aperture of the beam deflector 14 is square, and the emitter 8 provides an optical signal 11 that has an elliptical shape. In this example, the collimator C can include cylindrical lenses to accommodate the square optical aperture $A_{SQ}$ of the beam deflector 14. While examples of collimators C that include spherical and/or cylindrical lenses have been provided for the purpose of illustration, the collimator C can alternatively include any suitable device, element or system that provides a sufficient collimation of the optical beam B1 for deflection of the optical beam B1 by the beam deflector 14. The collimator C can also include any suitable device, element or system for shaping of the optical beam B1 to accommodate the optical aperture of the beam deflector 14.

The beam deflector 14 deflects, or changes the direction of, an applied signal, such as the optical beam B1, to provide a corresponding deflected beam B2. According to one embodiment of the present invention, shown in FIG. 2, the beam deflector 14 includes an acousto-optic deflector. Acousto-optic deflectors are known in the art and are available from a variety of sources, including Crystal Technologies, Inc., for example. The acousto-optic deflector deflects the optical beam B1 according to a control signal 15 by a deflection angle f based on the relationship Df=l(Df/Va), where l is the optical wavelength of the optical beam B1, Df is the frequency bandwidth of the acousto-optic deflector, and Va is the acoustic velocity of the acousto-optic deflector. This relationship indicates that the acousto-optic deflector deflects the optical beam B1 in proportion to the frequency f of the control signal applied to the acousto-optic deflector. In the example shown in FIG. 2, a function generator, voltage controlled oscillator (VCO), or other signal source drives the acousto-optic deflector by providing a control signal that is swept, tuned, or otherwise adjusted in frequency f over a frequency range between a frequency f1 and a frequency f2. In one example, an optical beam B1 incident on the acousto-optic deflector at an incidence angle of 0.45 degrees provides deflected beams B2 over a range of deflection angles Df of 2.9 degrees in response to an applied control signal 15 within the frequency range of 35 MHz-70 MHz.

According to alternative embodiments of the present invention, the beam deflector 14 includes a MEMS device (not shown) that has one or more optical reflectors or other devices that provide deflected beams B2 over a range of deflection angles. Typically, the MEMS device includes a focusing element to focus the optical beam B1 provided by the optical source onto one or more reflectors in the MEMS device. A collimating element can then be cascaded with the one or more reflectors in the MEMS device to provide deflected beams B2 that are collimated. The deflection angles of the deflected beams B2 provided by the MEMS device are established according to a control signal, applied to the MEMS device, which causes rotation of the one or more reflectors of the MEMS device.

The imaging telescope 16 receives the deflected beams B2 over a range Df of deflection angles f that are provided by the beam deflector 14 and directs the deflected beams B2 to the target T. Typically, the target T is proximate to a transducing interface 17 of an SPR transducer 18, at a transducing interface 17 of an SPR transducer 18, or the target T is otherwise associated with a transducing interface 17 of an SPR transducer 18. The target T typically contains one or more designated regions or samples for illumination. SPR transducers are known in the art and are shown in references such as *Characterization and Optimization of a Real-Time, Parallel, Label-Free, Polypyrrole-Based DNA Sensor by Surface Plasmon Resonance Imaging*, by Guedon et al., Analytical Chemistry, Vol. 72, No. 24, Dec. 15, 2000, pages 6003-6009.

The deflected beams B2 that are directed by the imaging telescope 16 result in incident beams B3 that illuminate the target T. The action of the beam deflector 14 and the imaging telescope 16 enable the target T, to be illuminated at a fixed position or location, that is independent of the angle of incidence of the incident beam B3. Thus, the angle of incidence of the incident beam B3 can be swept, tuned, varied, or otherwise adjusted via the action of the beam deflector 14, and directed to a target T via the action of the imaging telescope 16, so that the illumination provided by the resulting incident beam B3 is fixed in location or position due to the adjustment of the angle of incidence of the incident beam B3. The imaging telescope 16 maps the deflection angles f of the deflected beam B2 that are within a designated range Df, to corresponding incident angles $F_{INC}$ that are within a corresponding range DF to provide the incident beam B3. The incident beam B3 illuminates the target T at a fixed position when the incident angles $F_{INC}$ of the incident optical beam B3 are within the range DF.

Typically, the imaging telescope 16 includes a cascaded series of two or more lenses. The imaging telescope 16 magnifies the size of the deflected beam B2, based on selection of the focal lengths of the two or more lenses included in the imaging telescope 16 to adjust the size the illumination spot provided by the incident beam B3 at the target T. The magnification provided by the imaging telescope 16 can reduce or increase the size of the incident optical beam B3 relative to the size of the deflected beam B2. For example, if a first lens L1 has a focal length F1, and a second lens L2 has a focal length F2, a magnification to the size of the deflected beam B2 by a factor F2/F1 can be achieved for the incident beam B3 by the imaging telescope 16. When the focal length F2 is greater than the focal length F1, the incident beam B3 is larger than the deflected beam B2. When the focal length F1 is greater than the focal length F2, the incident beam B2 is larger than the deflected beam B3. FIG. 2 shows an example wherein the imaging telescope 16 includes two spherical lenses that provide uniform magnification across the deflected beam B2. Cylindrical lenses can also be included in the imaging telescope 16 to provide magnification to vary the size of the deflected beam B2 along an axis of the incident beam B3 that is established by the orientation of the cylindrical lenses. For example, a first pair of cylindrical lenses can provide a first magnification along a first axis perpendicular to the direction of propagation of the deflected beam B2, while a second pair of cylindrical lenses orthogonal to the first pair of cylindrical lenses can provide a second magnification along a second axis perpendicular to the first axis and perpendicular to the direction of propagation of the deflected beam B2.

The imaging telescope 16 also enables the incidence angle of the incident beam B3 at the target T to be a multiple of the deflection angle f of the optical beam B2. A multiplication factor relates the deflection angle f of the deflected beam B2 to the incidence angle $F_{INC}$ of the incident optical beam B3. The range $DF_{INC}$ of incident angles $F_{INC}$ can be greater than, less than, or equal to the range Df of deflection angles f. For example, when the beam deflector 14 provides deflected beams B2 over a range of angles of 2.9 degrees, a magnification factor of two provided by the imaging telescope 16 correspondingly multiplies the range of incidence angles $F_{INC}$ to 5.8 degrees, provided that the magnification is in the plane that includes the deflection angle f.

The multiplication provided by the imaging telescope 16 can be selected based on a designated range of incidence angles at the target T, the size and shape of the target T, a nominal angle of incidence at the target T, and a range Df of deflection angles f. In one example, for a range $DF_{INC}$ of incident angles $F_{INC}$ of 5.8 degrees, a nominal incidence angle of 65 degrees, a spot size of 14 mm, and a range range Df of deflection angles f of 2.9 degrees, a multiplication of two is suitable and can be achieved via the factor F2/F1. However, the magnification or multiplication provided by the imaging telescope 16 can also be selected according to the size, type and orientation of the optical devices, elements, or systems included in the imaging telescope 16. The imaging telescope 16 also maintains collimation of the deflected beam B2 at the incident beam B3.

In a typical application of the measurement system 10, a detector 20 intercepts a reflected optical signal B4 from the target T. The detector 20 is in signal communication with the target T, detecting an intensity of the reflected optical signal B4 as the incident angle $F_{INC}$ of the incident optical beam B3 is swept, tuned or otherwise adjusted over the range $DF_{INC}$ of incident angles $F_{INC}$ that is provided by the sweeping, tuning or adjusting of the deflection angle of the deflected beam B2 and the multiplication or magnitude provided by the imaging telescope 16. The detector 20 is typically a device, element or system, or an array of devices, elements or systems, that convert detected optical intensities to corresponding electrical signals. In one example, the detector 20 includes one or more Si, In GaAs, or Ge detection elements.

A processor 22 coupled to the detector 20 synchronizes the adjustment of the incidence angles $F_{INC}$ via the control signal 15 that is applied to the beam deflector 14. The processor 22 can also process the detected intensity of the reflected beam B4 to provide an SPR sensorgram 23 or other output that indicates a shift in resonant incidence angle $F_{RES}$ associated with the target T. FIG. 5A shows one example of the detected intensity of the reflected beam B4 indicating DF a shift in resonant incidence angle $F_{RES}$ induced by a change in refractive index of the target T. FIG. 5B shows one example of an SPR sensorgram 23 provided by the measurement system 10, indicating refractive index shown in micro-refractive index units ($10^{-6}$ RIU).

Since the target T can contain one or more designated regions or samples for illumination, a lens or other imaging element 24 can be interposed between the target T and the detector 20 to image the one or more designated regions or samples of the target T to corresponding positions on the detector 20. This enables the measurement system 10 to measure shifts in resonant incident angle, or corresponding shifts in refractive indices of multiple samples or regions at a transducing interface 17 of an SPR transducer 18, either in parallel or sequentially.

While a single measurement system 10 is shown in FIG. 2, alternative embodiments of the present invention can include two or more measurement systems 10 that illuminate a single target T. In these embodiments, each of the measurement systems 10 can operate at a different optical wavelength. In one example, two measurement systems 10 illuminate a target T wherein one of the measurement systems operates at an optical wavelength of 700 nm and the other of the measurement systems operates at an optical wavelength of 1600 nm.

A polarizer P is shown included in the propagation path of the reflected beam B4 to designate the polarization state of the reflected beam B4. Alternatively, polarizers can be included in the propagation paths of any of the other beams B1-B4. The measurement system 10 can also include beam splitters and optical detection elements at various locations in the optical propagation paths to monitor one or more of the beams B1-B4 for calibration of the measurement system 10. In the example shown in FIG. 2, an optionally-included half-wave plate l/2 is shown interposed between the beam deflector 14 and the imaging telescope 16 to align the polarization of the incident beam B3 at the target T. When the target T is associated with the transducing interface 17 of an SPR transducer 18, the half-wave plate l/2 provides a p-polarization of the incident beam B3 at the target T.

Figure 6:
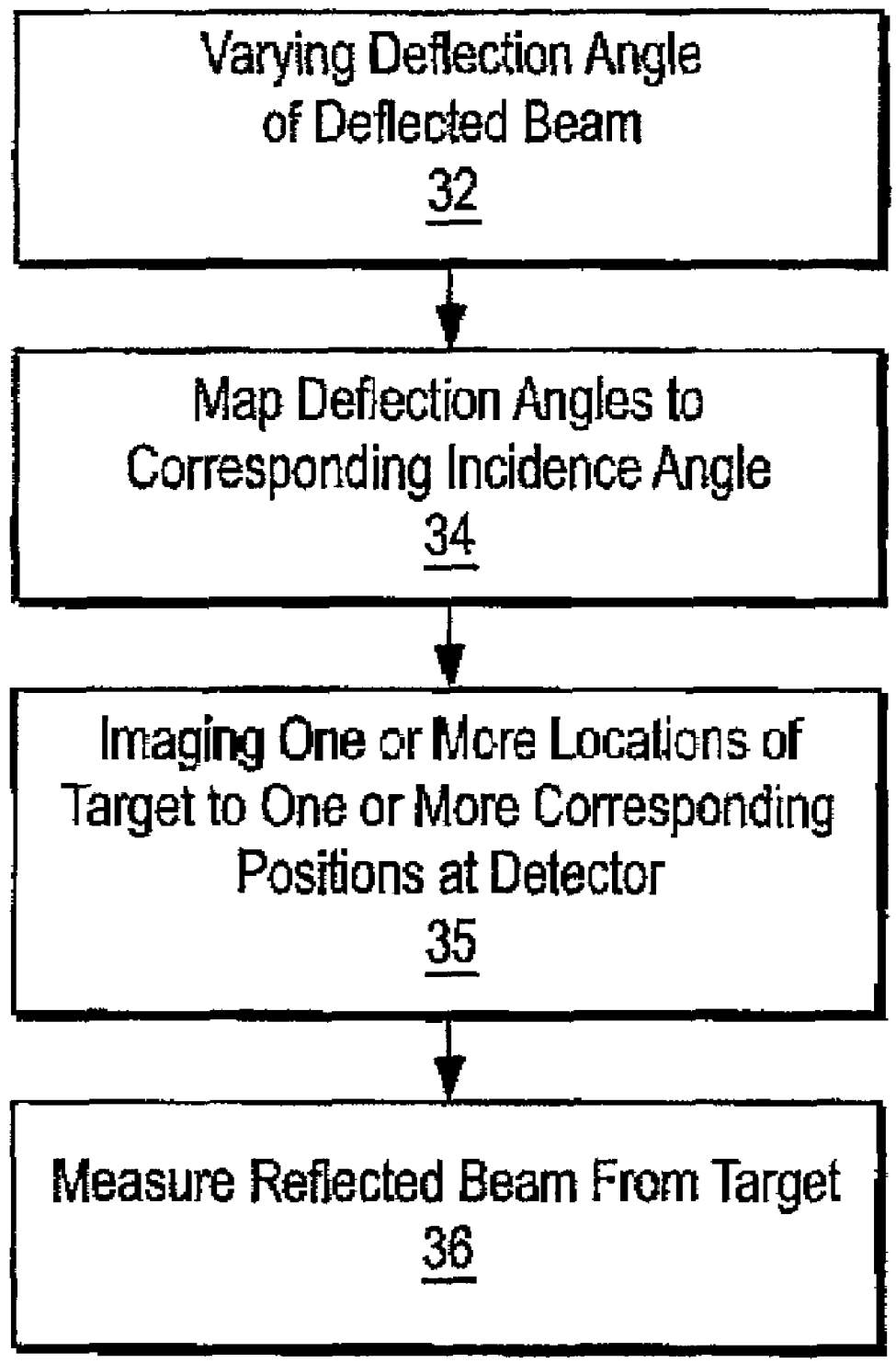
FIG. 6 shows a flow diagram of a swept-angle SPR measurement system implemented as a method, according to alternative embodiments of the present invention.

According to alternative embodiments of the present invention, the swept-angle SPR measurement system 10 is implemented according to a method 30 shown that is shown in the flow diagram of FIG. 6. The method 30 includes varying the deflection angle f of the deflected beam B2 within a range of deflection angles Df (step 32). The deflected beam B2 results from applying the optical beam B1 provided by the optical source 12 to the beam deflector 14 and sweeping, tuning or otherwise adjusting the deflection angle f of the deflected beam B2 via the control signal 15 applied to the beam deflector 14.

The method 30 then includes mapping the deflection angles f of the deflected beam B2 that are within the range Df of deflection angles f to corresponding incidence angles $F_{INC}$ within a corresponding range $DF_{INC}$ of incidence angles $F_{INC}$ to provide the incident beam B3 that illuminates the target T (step 34). The target T has a fixed position when the incident angle is within the range of incidence angles.

The method 30 then includes measuring the reflected beam B4 from the target T as the incidence angle $F_{INC}$ of the optical beam B3 at the target T is varied within the range $DF_{INC}$ of incidence angles $F_{INC}$ (step 36). Measuring the reflected beam B4 from the target T typically includes detecting the intensity of the reflected beam B4 and processing the detected intensity to provide an SPR sensorgram 23.

Optional step 35 includes imaging one or more locations of the target T to one or more corresponding positions at a detector 20.

While the embodiments of the present invention have been illustrated in detail, it should be apparent that modifications and adaptations to these embodiments may occur to one skilled in the art without departing from the scope of the present invention as set forth in the following claims.

The invention claimed is:

1. A measurement system, comprising:
an imaging telescope interposed between a fixed target and a beam deflector that provides a collimated deflected beam over a swept range of deflection angles, the imaging telescope mapping the collimated deflected beam to a collimated incident beam that illuminates the fixed target within a range of incidence angles that corresponds to the swept range of deflection angles, the fixed target including multiple samples for illumination by the collimated incident beam.

2. The measurement system of claim 1 wherein the imaging telescope includes at least two lenses enabled to modify at least one of a beam shape and a beam size of the collimated deflected beam provided by the beam deflector to establish at least one of a beam shape and a beam size of the collimated incident beam on the fixed target.

3. The measurement system of claim 1 further comprising a detector and an imaging element interposed between the fixed target and the detector, the imaging element imaging the multiple samples of the fixed target to corresponding positions on the detector.

4. The measurement system of claim 1 wherein the collimated incident beam is collimated only in a direction parallel to a plane that contains the range of incidence angles.

5. The measurement system of claim 1 further comprising a collimator interposed between the beam deflector and an optical source illuminating the beam deflector, the collimator transforming a beam shape provided by the optical source to accommodate an optical aperture of the beam deflector.

6. The measurement system of claim 5 wherein the collimator collimates the incident beam only in a direction that includes a plane containing the range of incidence angles.

7. The measurement system of claim 1 further comprising a half-wave plate interposed between the beam deflector and the imaging telescope, the half-wave plate providing a p-polarization of the collimated incident beam at the fixed target.

8. The measurement system of claim 1 wherein the beam deflector includes at least one of an acousto-optic deflector and a MEMS device.

9. The measurement system of claim 3 wherein each of the multiple samples includes an SPR transducer, and wherein the detector provides for parallel measurement of corresponding shifts in resonant incident angle at a transducer interface of each of the SPR transducers.

10. The measurement system of claim 3 wherein each of the multiple samples includes an SPR transducer, and wherein the detector provides for parallel measurement of corresponding shifts in refractive indices at a transducer interface of each of the SPR transducers.

11. A measurement system, comprising:
an imaging telescope interposed between a fixed target and a beam deflector that provides a collimated deflected beam over a swept range of deflection angles, the imaging telescope mapping the collimated deflected beam to a collimated incident beam that illuminates one or more designated regions of the fixed target at a uniform incidence angle at each incidence angle within a swept range of incidence angles, the swept range of incidence angles corresponding to the swept range of deflection angles.

12. The measurement system of claim 11 further comprising a detector and an imaging element interposed between the fixed target and the detector, the imaging element imaging each of the one or more designated regions of the fixed target to a corresponding position of the detector.

13. The measurement system of claim 12 wherein each of the one or more designated regions includes an SPR transducer, and wherein the detector provides for parallel measurement of corresponding shifts in resonant incident angle at a transducer interface of each of the SPR transducers included in the one or more designated regions.

14. The measurement system of claim 12 wherein each of the one or more designated regions includes an SPR transducer, and wherein the detector provides for parallel measurement of corresponding shifts in refractive indices at a transducer interface of each of the SPR transducers included in the one or more designated regions.

15. The measurement system of claim 11 wherein the imaging telescope includes at least two lenses enabled to modify at least one of a beam shape and a beam size of the collimated deflected beam provided by the beam deflector to establish at least one of a beam shape and a beam size of the collimated incident beam on the fixed target.

16. The measurement system of claim 11 further comprising a collimator interposed between the beam deflector and an optical source illuminating the beam deflector, the collimator transforming a beam shape provided by the optical source to accommodate an optical aperture of the beam deflector and collimating the incident beam only in a direction parallel to a plane that contains the range of incidence angles.

17. A measurement method, comprising:
sweeping a collimated deflected beam over a range of deflection angles;
mapping the collimated deflected beam with an imaging telescope to provide a collimated incident beam that has a swept range of incidence angles corresponding to the swept range of deflection angles, the collimated incident beam illuminating one or more regions of a fixed target over the swept range of incidence angles; and
imaging the one or more regions of the fixed target to a detector.

18. The measurement system of claim 17 wherein each of the multiple samples includes an SPR transducer, and wherein the detector provides for parallel measurement of corresponding shifts in resonant incident angle at a transducer interface of each of the SPR transducers.

19. The measurement system of claim 17 wherein each of the multiple samples includes an SPR transducer, and wherein the detector provides for parallel measurement of corresponding shifts in refractive indices at a transducer interface of each of the SPR transducers.

20. The measurement system of claim 17 wherein collimated incident beam is collimated only in a direction parallel to a plane that contains the range of incidence angles.

* * * * *